United States Patent [19]

Sabee

[11] Patent Number: 4,557,777
[45] Date of Patent: Dec. 10, 1985

[54] METHOD OF MAKING FORM FIT DIAPER WITH INSIDE SEAL AND THICKENED CROTCH

[76] Inventor: Reinhardt N. Sabee, 728 S. Summit St., Appleton, Wis. 54911

[21] Appl. No.: 530,512

[22] Filed: Sep. 9, 1983

Related U.S. Application Data

[62] Division of Ser. No. 244,442, Mar. 16, 1981, Pat. No. 4,410,324.

[51] Int. Cl.⁴ ..................... A61F 13/16; A61F 13/18; B32B 31/18
[52] U.S. Cl. .................................. 156/201; 156/202; 156/204; 156/227; 156/250; 156/256; 156/268; 604/358; 604/365; 604/368
[58] Field of Search .............. 156/201, 202, 204, 211, 156/227, 250, 256, 268; 604/358, 365, 368, 374

[56] References Cited

U.S. PATENT DOCUMENTS

| | | | |
|---|---|---|---|
| 2,295,439 | 9/1942 | Voigtman | 604/368 |
| 3,651,809 | 3/1972 | Champaigne | 604/368 |
| 3,746,592 | 7/1973 | Nystrand et al. | 156/201 |
| 3,984,272 | 10/1976 | Teed | 156/201 |

*Primary Examiner*—Caleb Weston
*Attorney, Agent, or Firm*—Fuller, House & Hohenfeldt

[57] ABSTRACT

A form fit disposable diaper has an absorbent pad folded intermediate the ends to provide increased absorbent material in the crotch and has water impervious side seal strips folded over the pad in the crotch to minimize leakage along the edges of the diaper and to prevent the absorbent pad from shifting. A quantity of water absorbent polymer is employed to enhance moisture absorbing capabilities. The side seal strips are desirably perforated to permit moisture strike through into the pad but prevent transfer of the polymer to the facing sheet and the skin of the diaper wearer.

3 Claims, 32 Drawing Figures

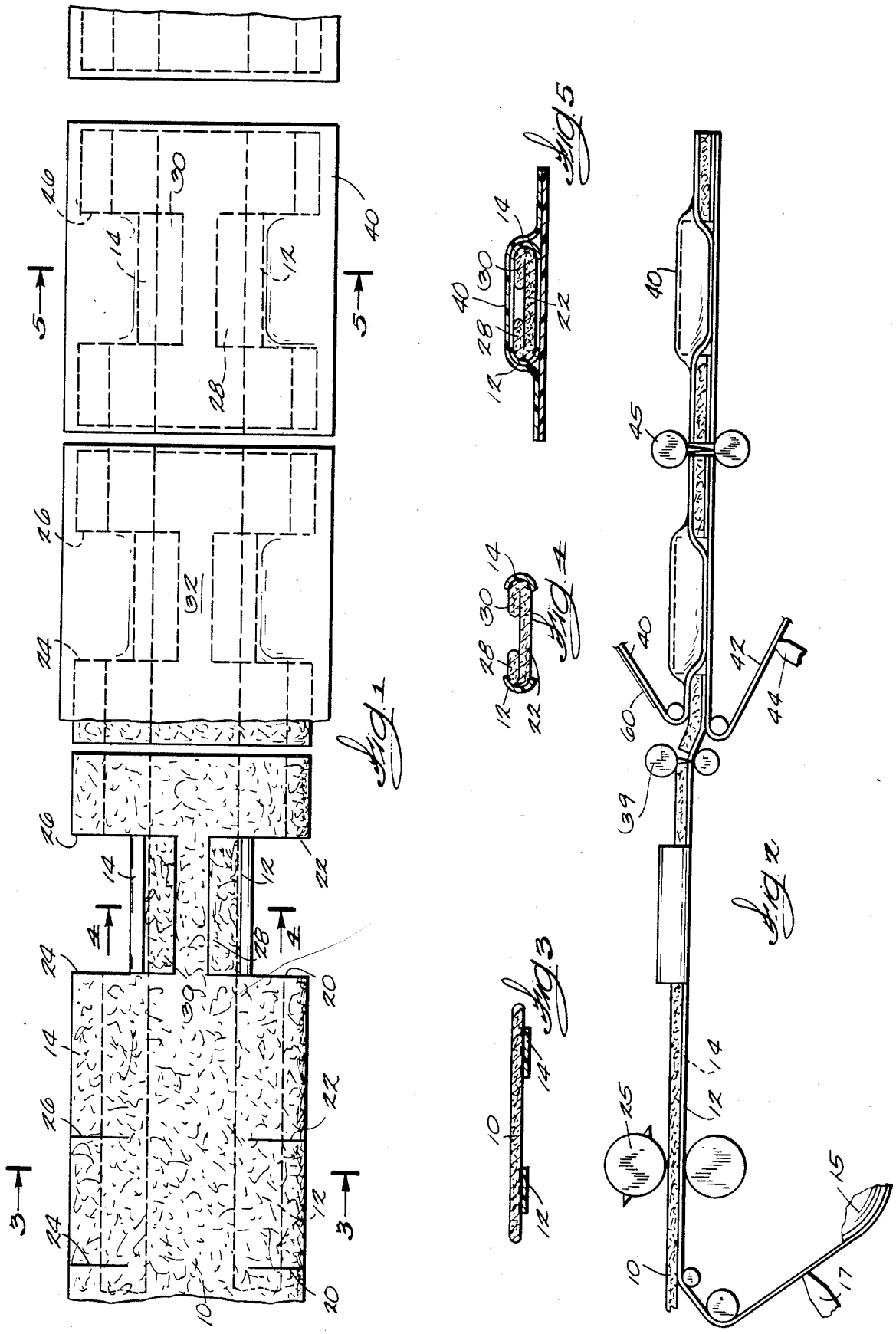

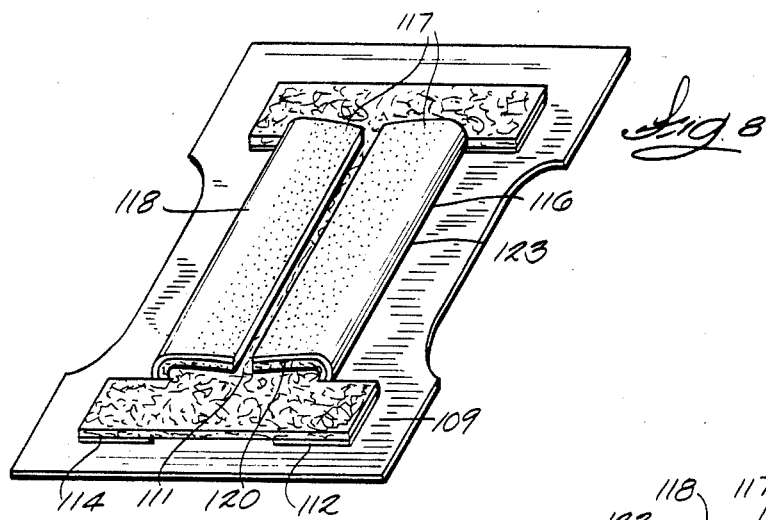
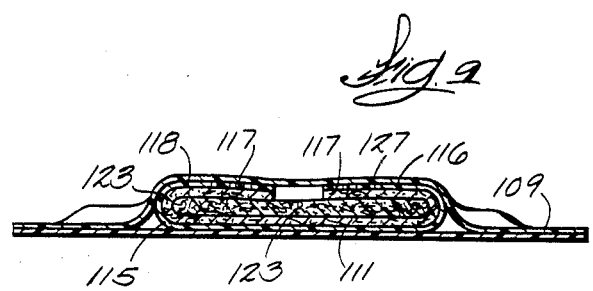
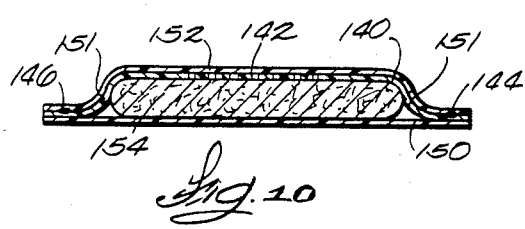
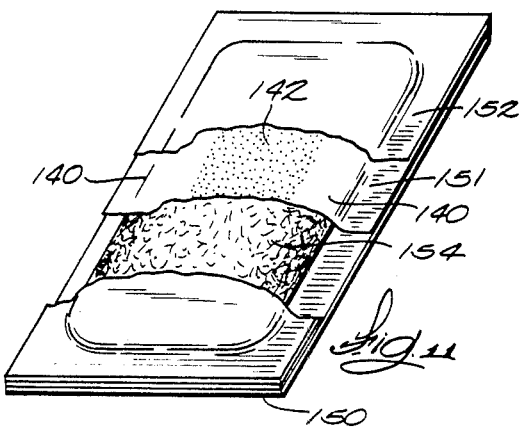
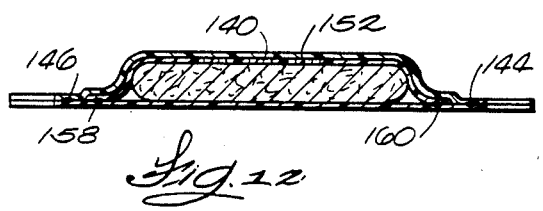
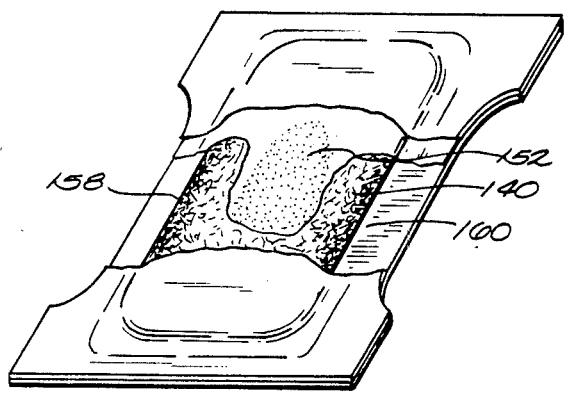

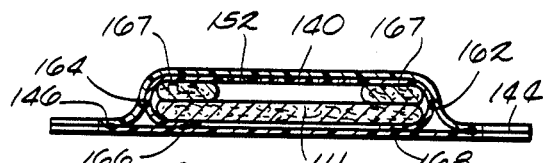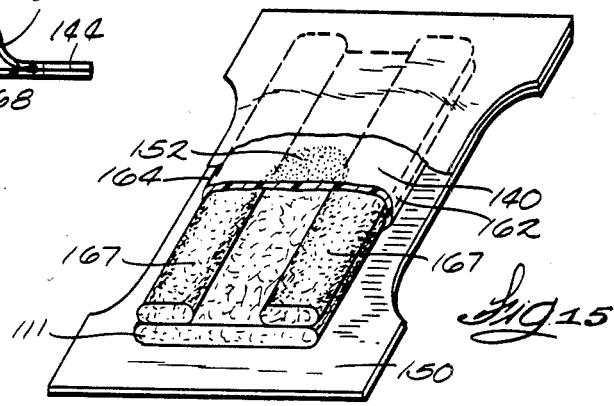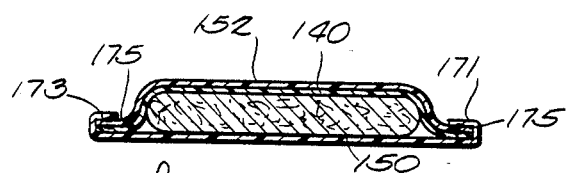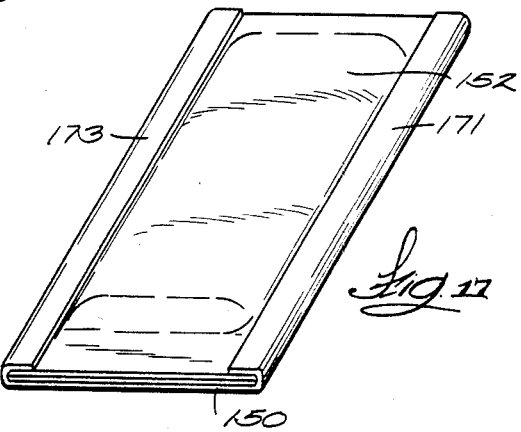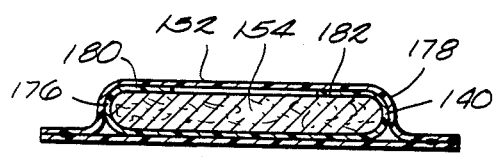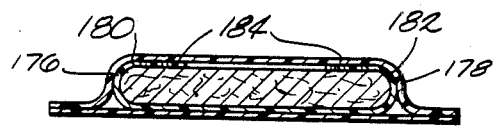

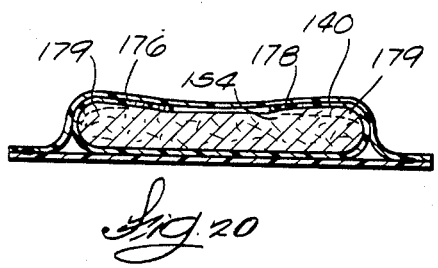
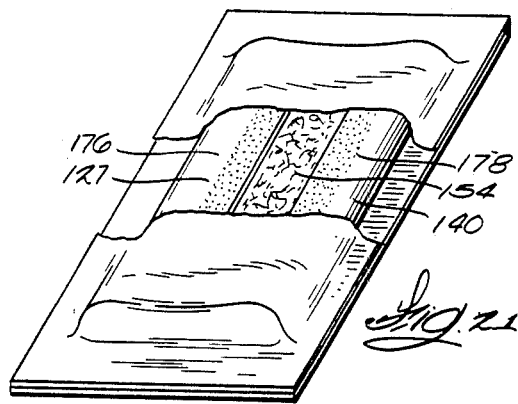
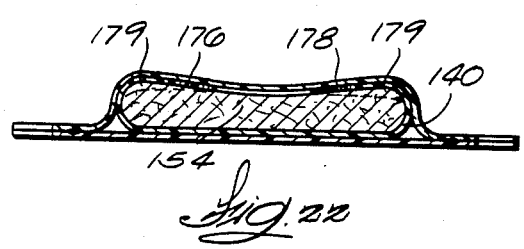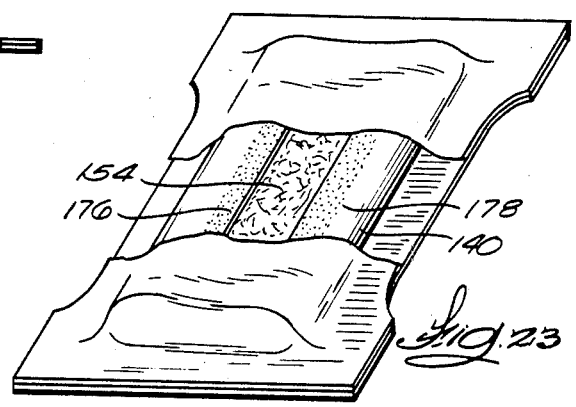
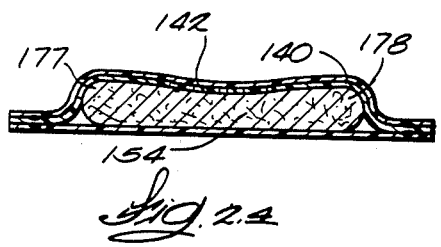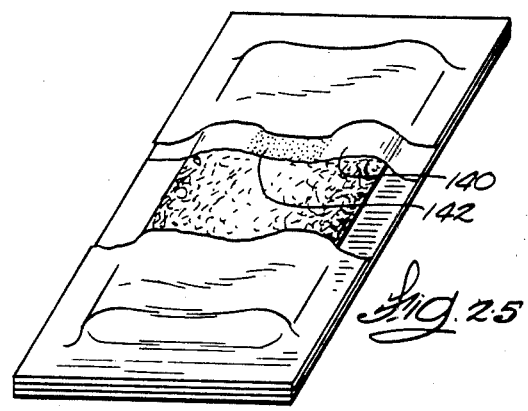

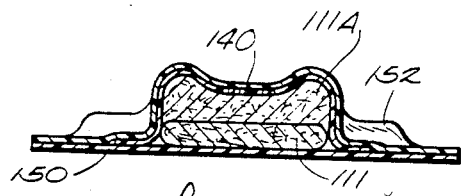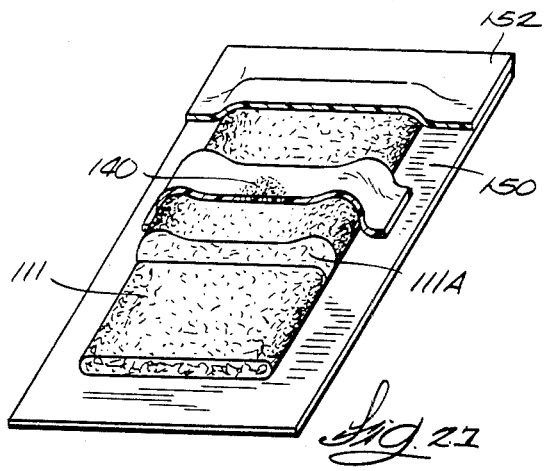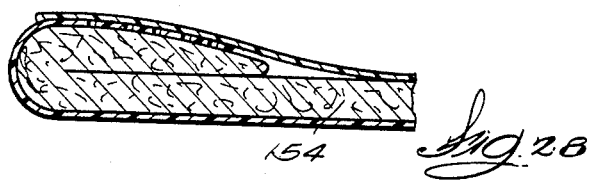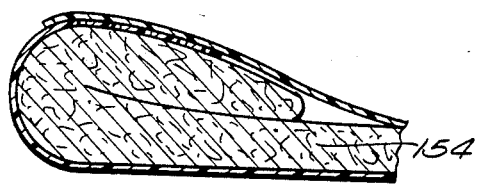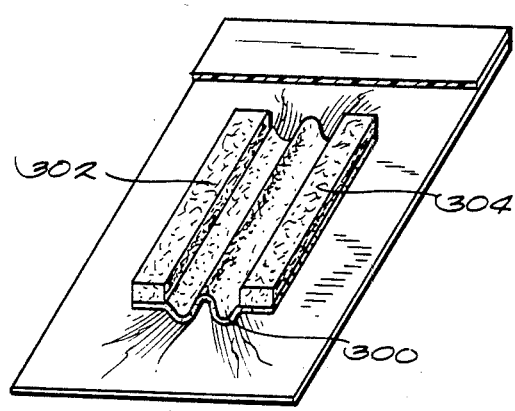

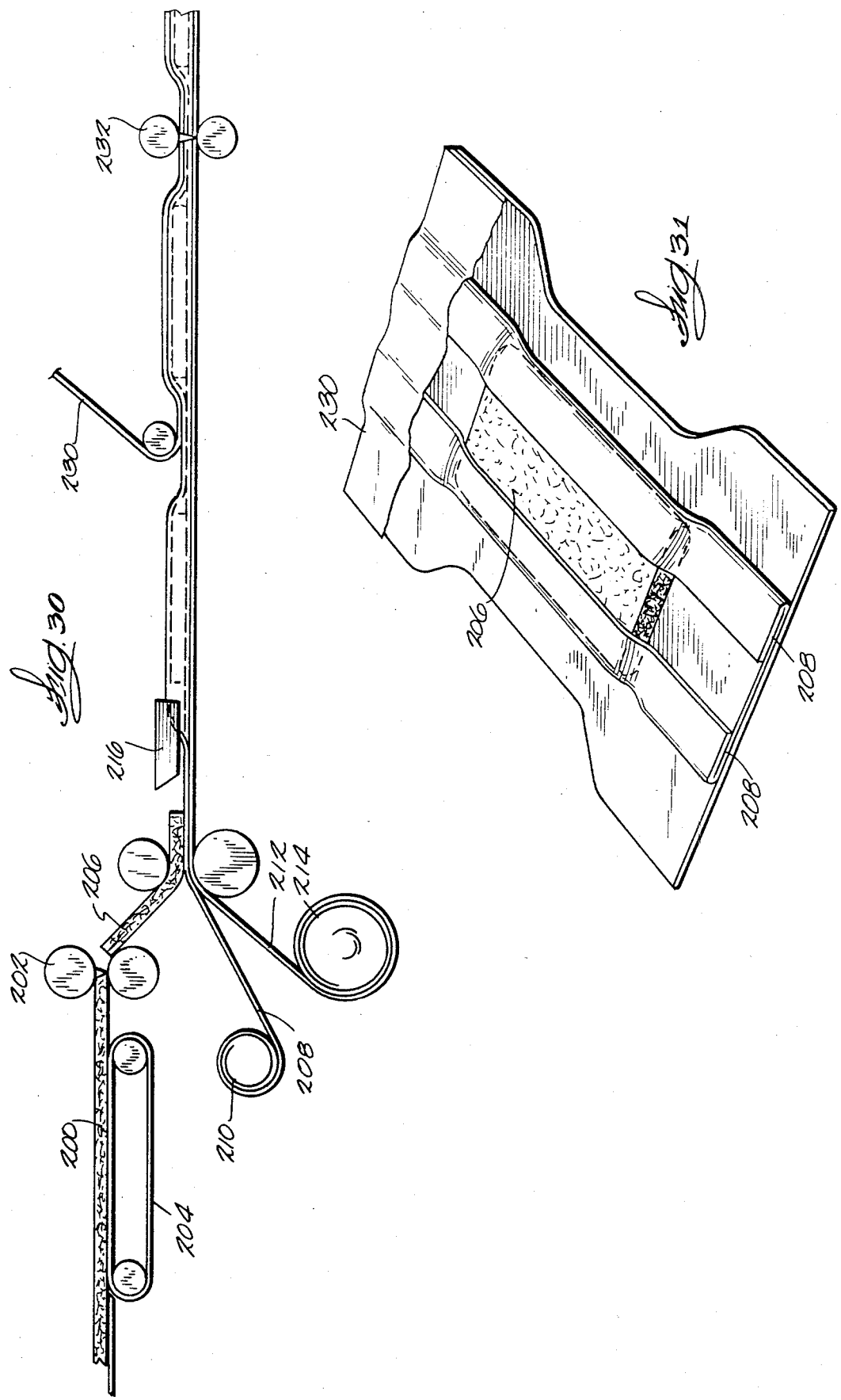

METHOD OF MAKING FORM FIT DIAPER WITH INSIDE SEAL AND THICKENED CROTCH

This is a division, of application Ser. No. 244,442, filed Mar. 16, 1981, U.S. Pat. No. 4,410,324.

BACKGROUND OF THE INVENTION

The preferred disposable diaper construction provides good fluid retention without leakage, the pad does not shift or disintegrate in use and the diaper does not feel uncomfortable on the skin. In addition, the preferred diaper does not cause excess wet contact with the skin which tends to macerate the skin, reducing its ability to resist diaper rash or irritation. Diapers employing elastic bands to hold the diaper tightly against the baby's legs helps stop side leakage. The elastic bands, however, greatly increase the cost of the diapers. U. S. Pat. Nos. 3,860,003 and 4,050,462 are illustrative of diaper constructions with elastic bands. My U.S. Pat. No. 4,227,952 illustrates a method and apparatus for making diapers with elastic bands.

Various diaper constructions have also been developed which employ hydrocolloidal material to increase moisture absorbency. One of the drawbacks of this construction has been the slippery, uncomfortable feeling of this material to the wearer of the diapers.

Diaper constructions have also been developed with water impervious side seals to prevent leakage from the absorbent pad along the side margins of the diaper. Sabee U.S. Pat. No. 3,386,442 discloses the use of separate plastic strips along the side margins of the diaper to serve as a side seal. The plastic strips of this type of construction, however, contact the skin and cause chafing of the skin of the wearer of the diaper.

SUMMARY OF THE INVENTION

The present invention provides a disposable diaper construction in which various of the drawbacks and disadvantages of prior art diapers are overcome. Leakage is minimized by providing an auxiliary seal along the side edges of the pad, with the sealing sheet located beneath a comfortable, porous facing sheet and spaced inwardly from the side margins of the diaper. Positioning the seal on the side edges of the pad under the facing sheet prevent it from coming in contact with the wearer's skin, thus avoiding chafing and irritation caused by contact of the plastic film typically used for the water impervious parts of a diaper. The side margins of the absorbent pads are free to open or expand as they absorb the body fluids. Various absorbent materials having different absorbent properties can be employed with this seal construction. Examples are wood cellulose fibers and hydrocolloidal absorbent materials. The side seals also hold the pad in place so that it does not shift or disintegrate during use. This insures that the pad is positively positioned as intended, to maximize protection.

The absorbent pad assembly may have thicker margins spaced apart by a thinner central area which will result in differential expansion of the margins to a greater degree than the central area when becoming wet, which enhances the seal against the baby's legs. The thinner central area being more flexible will allow the diaper to conform better to various body shapes. This combined with the thicker side margins under an expandable seal reduces to a minimum the spill-over which occurs during flooding conditions.

The side seal strips are desirably perforated if they are wide to enable strike through of moisture through the water impervious sealing strip portions which face the infant or user of the diaper. The perforated water impervious strips will prevent contact of the hydrocolloidal material with the user's skin and hence avoid the unpleasant feeling associated with contact of such materials. An intermediate sealing sheet may also be used which has perforations at least in the crotch area. This sheet will allow fast strike through in the crotch area and allow wicking to the remainder of the absorbent pad under the sealing sheet where it cannot contact the skin of the wearer and become an irritant. Moisture trapped against the skin can cause irritation.

The diaper and method of the invention can employ two spaced water impervious ribbons upon which the absorbent pad is supported prior to assembly of the facing of the backing sheets. The pad and ribbons are simultaneously cut with transverse cuts to form the foldable pad flaps. The ribbon and pad flaps are then folded with the ribbon forming the edge side seals. The ribbon is provided with adhesive prior to the cutting and folding operation. The folded, adhesively secured ribbon also maintains the folds of the absorbent pad. Further objects and advantages of the invention will be apparent from the disclosure.

DESCRIPTION OF THE DRAWINGS

FIG. 1 is a plan view showing the method of making the diaper of the invention.

FIG. 2 is a side elevational view of the procedure in making the diaper.

FIG. 3 is a sectional view along line 3—3 of FIG. 1.

FIG. 4 is a view along line 4—4 of FIG. 1.

FIG. 5 is a view along line 5—5 of FIG. 1.

FIG. 8 is a perspective view of a diaper construction in which the side seal ribbons are perforated and have increased absorbency zones under the side seal ribbons.

FIG. 9 is a sectional view of a diaper similar to the diaper shown in FIG. 8 except the side seals are made of one piece construction with an auxiliary pad in the crotch area.

FIG. 10 is a sectional view of a diaper construction with a perforated sealing sheet which is sealingly connected to the top and bottom sheets at the same general point along the margins.

FIG. 11 is a perspective view of the diaper shown in FIG. 10.

FIG. 12 is a diaper construction of a diaper similar to that shown in FIG. 10 with the sealing sheet sealed to the backing sheet at a different point of contact for a form fit diaper.

FIG. 13 is a perspective view with portions removed of the diaper shown in FIG. 12.

FIG. 14 is a sectional view of a diaper construction in which the sealing sheet is tucked around beneath the absorbent pad and side margins containing auxiliary absorbent strips.

FIG. 15 is a perspective view of the diaper construction shown in FIG. 14.

FIG. 16 is a sectional view of a diaper construction in which the backing sheet is folded over the facing and sealing sheet.

FIG. 17 is a perspective view of the diaper construction shown in FIG. 16.

FIG. 18 is a sectional view of a diaper construction having a one piece sealing sheet having sides folded around and over the top of the absorbent pad.

FIG. 19 is a diaper construction similar to FIG. 18 in which the folded over sides of the sealing sheet are perforated.

FIG. 20 is a sectional view of a diaper construction in which increased absorbent material is located under the side margins of the sealing sheet.

FIG. 21 is a perspective view with parts removed of the diaper construction shown in FIG. 20.

FIG. 22 is a diaper construction of a diaper similar to FIG. 20, but of a form fit diaper.

FIG. 23 is a perspective view of the diaper construction shown in FIG. 22.

FIG. 24 is a diaper construction similar to the diaper shown in FIGS. 10 and 11 with increased thickness of absorbent material along the side margins in the crotch area.

FIG. 25 is a perspective view with parts removed of the diaper shown in FIG. 24.

FIG. 26 shows a diaper construction similar to the diaper in FIG. 12 with increased absorbent material in the margins under the sealing sheet.

FIG. 27 is a perspective view with parts removed of the diaper construction shown in FIG. 26.

FIG. 28 is an enlarged fragmentary sectional view of a diaper having the pad containing hydrocolloidal material folded over under the side seal.

FIG. 29 is a view similar to FIG. 28 with the pad expanded upon absorption of moisture.

FIG. 30 is a diagrammatic perspective view of a modified embodiment of the method of making diapers with ribbons which form edge seals.

FIG. 31 is a perspective view of a diaper made in accordance with the method of FIG. 30.

FIG. 32 is a fragmentary perspective view of a modified pad construction with a thin central web portion.

DESCRIPTION OF THE PREFERRED EMBODIMENT

Figure 6:
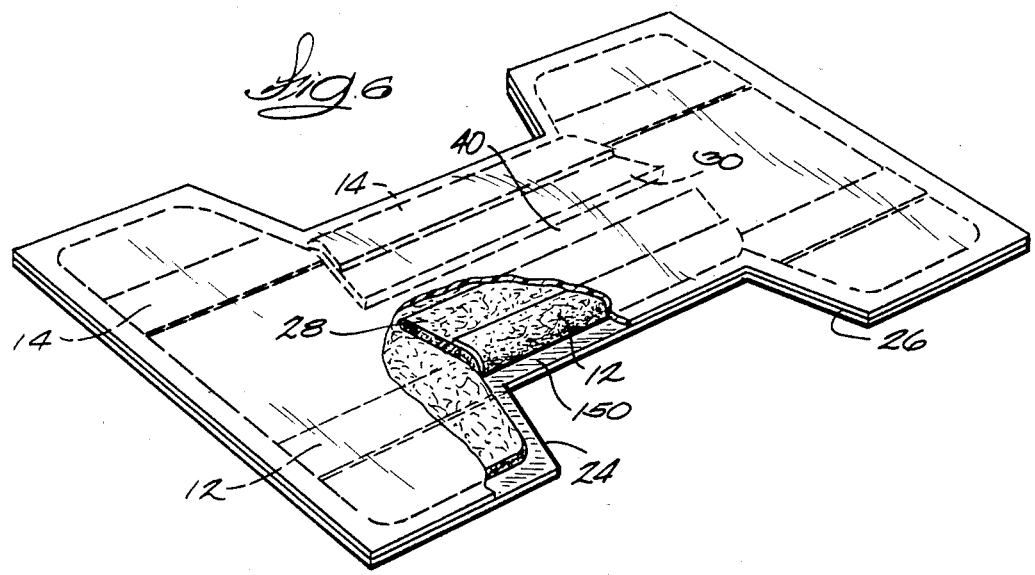
FIG. 6 is an enlarged perspective view with parts broken away of the diaper of the invention.

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

The diaper of the invention is best described by the method of making one embodiment thereof.

Referring to FIG. 1, the initial step of forming the diaper involves providing absorbent pad material 10 and supporting the pad 10 on continuous spaced water impervious plastic ribbons 12 and 14 supplied from parent rolls 15. As illustrated in FIG. 2, an adhesive is applied to the ribbons 12, 14 by the glue assembly 17 prior to application of the ribbons to the pad. Subsequently and simultaneously, the pad and part of the ribbons are cut by cuts 20, 22, 24 and 26 formed by a knife assembly 25 which may converge or be at 90° to the machine direction.

The cut portions of the pad and cut portions of the ribbons are folded over by conventional folding apparatus (not shown) to form side seals for the diaper. As illustrated in FIG. 4, the edges 28 and 30 of the absorbent pad can be folded over upon the mid portion 32 of the pad to provide increased absorbency. The folded over ribbons 12 and 14 are preferably adhesively secured to the pad and backing to maintain the folds and lock the pad in place to prevent the pad from shifting between the top and bottom sheets and prevent the pad from coming apart. Films having a high degree of cling characteristics will secure itself to a compatible backing without the need of adhesives, some of these films being high cling polyethylene or polypropylene, vinyldene chloride and various blends of ethylene vinyl acetate (EVA) resins, but not limited to these.

The folded over ribbons 12 and 14 may be adhesively secured to the pad, facing or backing to further insure that the folds are maintained and the pad locked in place to prevent the pad from shifting between the top and bottom sheets and to prevent the pad from disentegrating.

Subsequent to the folding over of the pad and ribbons, the pulp is cut off by a cut-off knife 39 and the top sheet 40 and the bottom sheet 42 are applied to the folded pad (FIG. 2). Adhesive is applied to either the top or bottom sheet, or both, by a glue applicator, such as applicator 44, to seal the edges of the top and bottom sheets and encapsulate the pad. The top and bottom sheets are then notched by a cutting assembly 45 so that these sheets are complementary in shape to the pad. The terms "plastic ribbons", "water impervious ribbons", "sealing strips" and "sealing sheet" are used interchangeably in this application.

Figure 7:
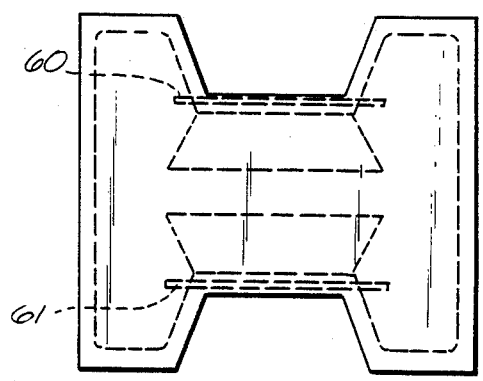
FIG. 7 is a perspective view of a modified embodiment of the diaper.

The top or bottom sheet can be provided with spaced elastic ribbons 60, 61 (FIG. 7) in the crotch area by a method described in my patent, or any other technique. The elastic ribbons are adhesively applied prior to assembly of both the top and bottom sheets.

After the top and bottom sheets are secured together, tabs are applied to complete the diaper.

FIG. 8 is illustrative of a diaper construction in which the ribbons 112 and 114 have inturned sealing portions 116 and 118 which seal the side edges of the pad 111 in the crotch area to prevent leakage. The ribbons 112, 114 have perforated zones 117 in the crotch area. Beneath the perforated zones 116 and 118 are increased absorbency zones provided by either folded over sides 120 of the pad 111, auxiliary pads or a quantity of hydrocolloid material.

As used herein, the term hydrocolloid material means any water insoluble hydrocolloid in any of its forms, whether it be a fiber, tape or powder or any substance that yields gels with water. This would include but is not limited to the following substances: (a) hydrolyzed starch polyacrylonitrile copolymer Hspan, Product 35-A-100, Grain Processing Corp., Muscatine, Iowa, disclosed in U.S. Pat. No. 3,661,815; (b) Product No. XD-8587.OIL, which is cross-linked, Dow Corning Chemical Co., Midland, Michigan; (c) Product No. SGP 502S, General Mills Chemical, Inc., Minneapolis, Minnesota; (d) Product No. 78-3710, National Starch and Chemical Corp., New York, N.Y.; (e) a hydrogel base product, Carbowax, a Trademark of Union Carbide Corp., Charleston, West Virginia; (f) base-saponified starchpolyacrylonitrile and graft copolymers, United States Department of Agriculture, Peoria, Illinois, disclosed in U.S. Pat. No. 3,425,971; (g) Aqualon C and Aqualon R water insoluble sodium (arboxymethyl cellulose fibers from Hercules; (h) absorbent starch based copolymer (starch-acrylonitrile); No. 35-A-100 polymer from Grain Processing Corp.; and (i) polyacrylamide polymers, such as XD-7343.01 from Dow Chemical are all suitable and any of the water insoluble absorbent polymers known as "super slurpers" in the trade.

These products are satisfactory for high fluid retention in the crotch area while being subjected to the normal flexing and pressures resulting from movements of a wearer. Absorbent polymers are also available in a film form and printed on or between two layers of absorbent tissue which can then be cut to shape and placed in the most effective area, such as inside the seals at the sides of the absorbent pad in the crotch area, other areas of the crotch area, or the total crotch area. Elastic bands may be attached to the sides of the diaper in the crotch area, at an increase in cost, to further insure confinement of flooding to the absorbents located in the crotch area. Fluff-pulp, which is used in diapers, has almost instantaneous uptake rate of liquids, because only a small percent of the liquid is absorbed in the fiber, with the remainder being held in the interstices of the fiber in the pad. It is extremely sensitive to pressure in that applied pressures squeeze fluids from the pad and into body contact where it becomes an irritant. Therefore, increasing the bulk in the sides of the absorbent pad will help instantaneous absorption but also subjects these sides to greater pressures and a greater squeezing action, causing a greater amount of body fluids to escape from inside the edge seals. The use of an absorbent polymer in the edge seal zones overcomes this problem. Such hydrocolloid materials have the capability of absorbing many times their weight in liquids and swell to form a gelatinous mass when wetted, and will not release this liquid when subjected to pressures from body movements.

Referring to FIG. 8, the sealing strips 112, 114 are preferably sealed to the backing sheet so that the inturned portions 116, 118 of the sealing strips lock the pad 111 against shifting between the bottom or backing sheet 109 and the facing sheet 127 (FIG. 9).

The perforated zones 117 permit moisture penetration through the perforations or openings in these zones and allow the hydrocolloid material to absorb the moisture. The perforated zones 117, however, will prevent communication of the hydrocolloid through the facing sheet which would provide a slippery and gelatinous feeling which is uncomfortable and undesirable. This undesirable feeling has been a drawback in the past in the use of hydrocolloids in diapers.

FIG. 9 is a diaper construction similar to FIG. 8. However, the inturned edge seal portions 116 and 118 are the side margins of the one piece sealing sheet 115 and are folded over an auxiliary pad 123.

FIGS. 10 through 27 show various modified embodiments using intermediate sealing sheets in between the facing and backing sheets to assist in locking the pad in place and to provide edge seals to prevent leakage from the sides of the absorbent pad and to provide an intermediate sealing sheet having perforations, slits or valvular openings, or being foraminous, to prevent transfer of the hydrocolloid back through the facing sheet. FIGS. 10 and 11 show a rectangular diaper construction in which an intermediate water impervious sealing sheet 140 has a perforated zone 142 in at least the crotch area, as shown in FIG. 11, and the intermediate sheet is sealed either by heat sealing or glue along the margins 144 and 146 to both the backing sheet 150 and facing sheet 152. The sheet portions 151 provide the seals for the absorbent pad 154.

FIGS. 12 and 13 show an intermediate water impervious sheet 140 with perforations 152 in the crotch area which is sealed along its lateral edges at 158, 160 at a point inwardly from the side edges of the backing and facing sheets, which are also sealed at 144 and 146. This type of seal is appropriate for the form fitting diaper.

FIGS. 14 and 15 show a diaper construction with an intermediate sealing sheet 140 in which the lateral edges are folded around and tucked under the absorbent pad by folds 162 and 164 and sealed to the backing sheet intermediate the edges of the diaper at 166 and 168. Auxiliary pad strips 167 are provided.

In FIGS. 16 and 17, the intermediate sealing sheet 140 is sealed to both the facing and backing sheets. The backing sheet 150 has edges 171 and 173 which are folded over the margins 175 of the facing sheet 152.

FIG. 18 shows an intermediate sealing sheet 140 having folds 176, 178 folded around and over on the top of the pad 154. FIG. 19 is similar to FIG. 18, but the inturned ends 180 and 182 are perforated at 184 in the crotch area to permit strike through of fluid from the top sheet.

FIGS. 20 through 29 show diaper constructions with increased pad thickness formed by either an extra pad or hydrocolloidal material at the margins of the diaper. When a hydrocolloid is used, swelling of this material when exposed to moisture tightens the diaper against the body to enhance the seal between the diaper and the body to prevent spill-over or loss of body fluids.

In FIGS. 20 and 21, an intermediate sealing sheet 140 is wrapped around the absorbent pad 154. Hydrocolloidal material 179 is located under the flaps 176 and 178. The diaper shown in FIGS. 22 and 23 is similar to that shown in FIG. 20, but is a form fitting diaper. The flaps 176, 178 can be perforated in the crotch.

The diaper construction illustrated in FIGS. 24 and 25 includes a sealing sheet 140 with a perforated zone 142 similar in construction to the diaper shown in FIGS. 10 and 11. However, this diaper has increased thickness of absorbent material along the side margins 177, 178 at least in the crotch area.

The diaper of FIGS. 26 and 27 has an auxiliary pad in the crotch area as well as the pad 111. It also includes a perforated sealing sheet 140. FIG. 29 shows the differential expansion of the pad 154 in comparison with FIG. 28 along the edges after being exposed to moisture as a result of a larger quantity of hydrocolloid at the longitudinal margins of the diaper rather than in the center of the diaper.

FIG. 30 bulk pad material 200 is delivered to a cut-off knife assembly 202 by conveyor 204. Discreet lengths 206 of pad material are cut off by the cut-off assembly 202 and delivered to a pair of spaced ribbons 208 supplied from parent rolls 210. The backing sheet 212 is supplied from a parent roll 214. After the pads 206 have been superimposed on the spaced ribbons 208, the ribbons are plow folded by plows 216 over the side edges of the pad 206, as shown in FIG. 31, to provide edge seals. After the ribbons are folded, the top sheet 230 is applied over the ribbons and pad and the diapers are subsequently cut from the web by a cutoff assembly 232. In this method, the ribbons are the full length of the diaper rather than the length of the pulp or pad as with the method illustrated in FIG. 1.

FIG. 32 illustrates a pad construction with a thin conformable web section 300 with thicker side margins 302, 304. The thin web section 300 collapses or "necks down" to enable the diaper to better conform to the body and maintain a close fit during body movements. The thick side margins 302 and 304 can include a greater concentration of hydrocolloidal material than the central crotch area.

I claim:

1. A method of making disposable diapers comprising the steps of securing an absorbent pad to spaced plastic ribbons, cutting portions of the pad, folding over the pad upon itself and portions of the ribbon over the pad, applying facing and backing sheets to the pad-ribbon assembly, thereby holding the folded ribbons in place, and cutting the backing and facing sheets to conform to the ribbon-pad configuration.

2. The method of claim 1 including the step of transversely cutting the ribbons through a portion of their width prior to folding the ribbons.

3. The method of claim 1 wherein said ribbons are the side margins of a one-piece sealing sheet.

* * * * *